United States Patent
Hannesson et al.

(10) Patent No.: US 12,419,762 B2
(45) Date of Patent: Sep. 23, 2025

(54) VENTILATED PROSTHETIC SOCKET AND KIT FOR MAKING THE SAME

(71) Applicant: Ossur Iceland ehf, Reykjavik (IS)

(72) Inventors: Sigurdur Hannesson, Reykjavik (IS); Oskar Thor Larusson, Reykjavik (IS); Margret Sol Ragnarsdottir, Reykjavik (IS); Dadi Granz, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 0 days.

(21) Appl. No.: 18/678,754

(22) Filed: May 30, 2024

(65) Prior Publication Data

US 2024/0307197 A1    Sep. 19, 2024

Related U.S. Application Data

(63) Continuation of application No. 17/519,969, filed on Nov. 5, 2021, now Pat. No. 12,029,665.

(60) Provisional application No. 63/110,732, filed on Nov. 6, 2020.

(51) Int. Cl.
    *A61F 2/80*    (2006.01)
    *A61F 2/50*    (2006.01)

(52) U.S. Cl.
    CPC .............. *A61F 2/80* (2013.01); *A61F 2/5044* (2013.01); *A61F 2002/802* (2013.01)

(58) Field of Classification Search
    CPC ........ A61F 2/70; A61F 2/78; A61F 2002/805; A42B 3/28; B01D 2273/10
    See application file for complete search history.

(56) References Cited

U.S. PATENT DOCUMENTS

| | | | |
|---|---|---|---|
| 2,530,285 | A | 11/1950 | Catranis |
| 2,833,305 | A | 5/1958 | Muckley et al. |
| 5,503,543 | A | 4/1996 | Laghi |
| 5,573,825 | A | 11/1996 | Brewster |
| 5,718,925 | A | 2/1998 | Kristinsson et al. |

(Continued)

FOREIGN PATENT DOCUMENTS

| | | |
|---|---|---|
| CN | 104757729 A | 7/2015 |
| CN | 108209005 A | 6/2018 |
| DE | 1082702 B | 6/1960 |

OTHER PUBLICATIONS

International Search Report and Written Opinion from PCT Application No. PCT/US2021/058211, mailed Apr. 7, 2022.

*Primary Examiner* — Christie Bahena
(74) *Attorney, Agent, or Firm* — Workman Nydegger

(57) ABSTRACT

A ventilated prosthetic socket includes a rigid, structural and load-bearing socket body forming an inner volume adapted to receive a residual limb, and a wall thickness extending from an inner wall surface bordering the inner volume to an outer wall surface. The socket body defines an opening extending through the wall thickness. At least one vent element communicates the inner wall surface to the outer wall surface and extending therebetween in the opening along the socket body to thereby permit a transfer of air from the inner volume to outside of the socket through the opening. The at least one vent element is separately formed from the socket body and discretely insertable into the opening and secured against the inner surface and the outer wall surface. A method and kit are provided to adapt the socket in a ventilated form.

15 Claims, 12 Drawing Sheets

(56) References Cited

U.S. PATENT DOCUMENTS

| | | |
|---|---|---|
| 5,885,509 A | 3/1999 | Kristinsson |
| 5,888,231 A | 3/1999 | Sandvig et al. |
| 5,971,729 A | 10/1999 | Kristinsson et al. |
| 5,972,036 A | 10/1999 | Kristinsson et al. |
| 5,980,577 A | 11/1999 | Radis et al. |
| 6,416,703 B1 | 7/2002 | Kristinsson et al. |
| 6,991,444 B1 | 1/2006 | Laghi |
| 7,438,843 B2 | 10/2008 | Asgeirsson |
| 9,474,635 B2 | 10/2016 | Egilsson et al. |
| 9,756,898 B2 | 9/2017 | Peikert et al. |
| 10,342,682 B2 | 7/2019 | Egilsson et al. |
| 10,420,657 B2 | 9/2019 | Jonsson et al. |
| 10,729,566 B2 | 8/2020 | Egilsson et al. |
| 2007/0265711 A1* | 11/2007 | Klein .................. A61F 2/7812 623/33 |
| 2009/0082877 A1 | 3/2009 | Einarsson |
| 2014/0259295 A1 | 9/2014 | Guglielmo et al. |
| 2018/0185176 A1 | 7/2018 | Jonsson et al. |
| 2020/0146850 A1 | 5/2020 | Asgeirsson et al. |

* cited by examiner

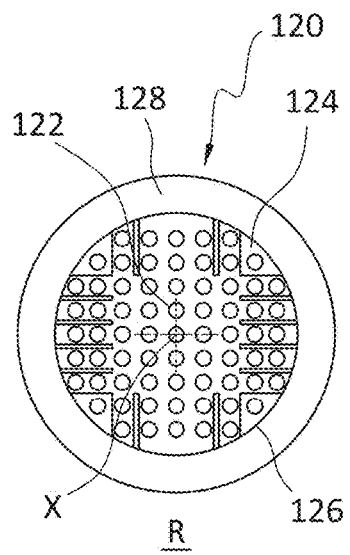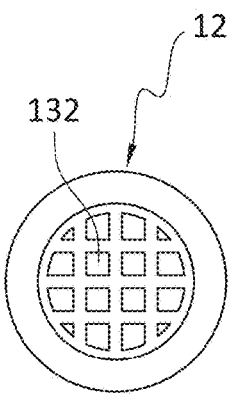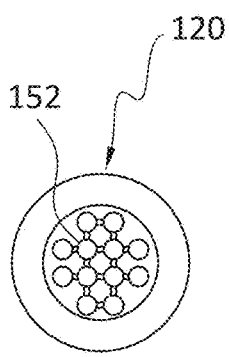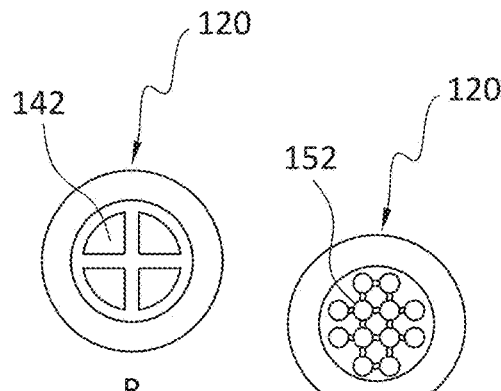
FIG. 2A  FIG. 2B  FIG. 2C  FIG. 2D
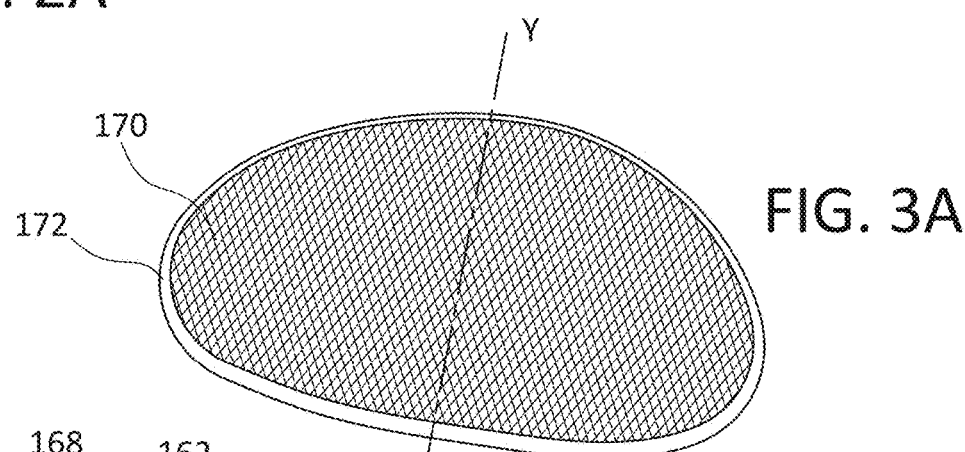
FIG. 3A
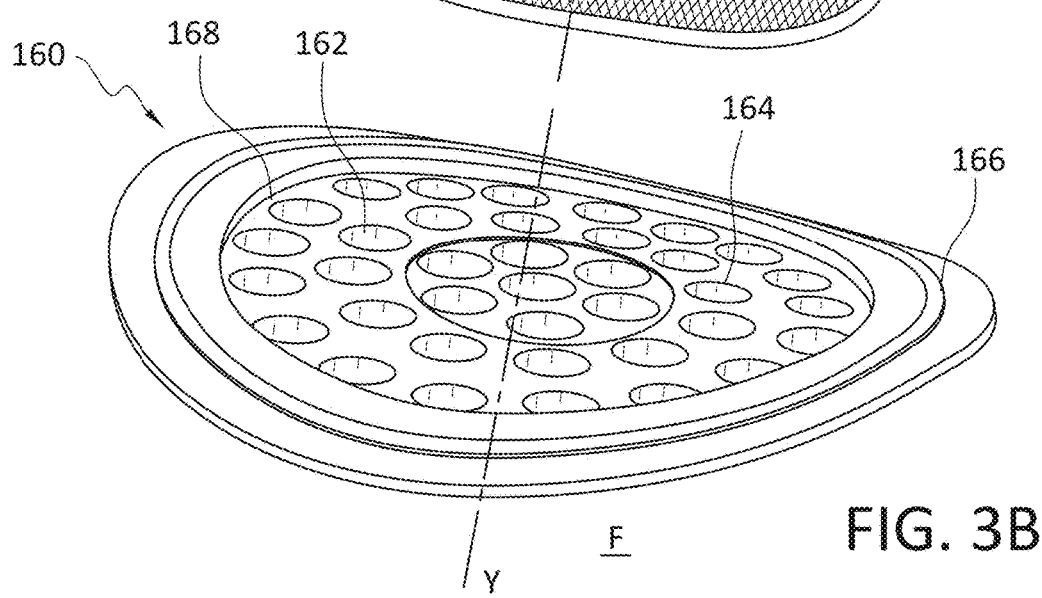
FIG. 3B

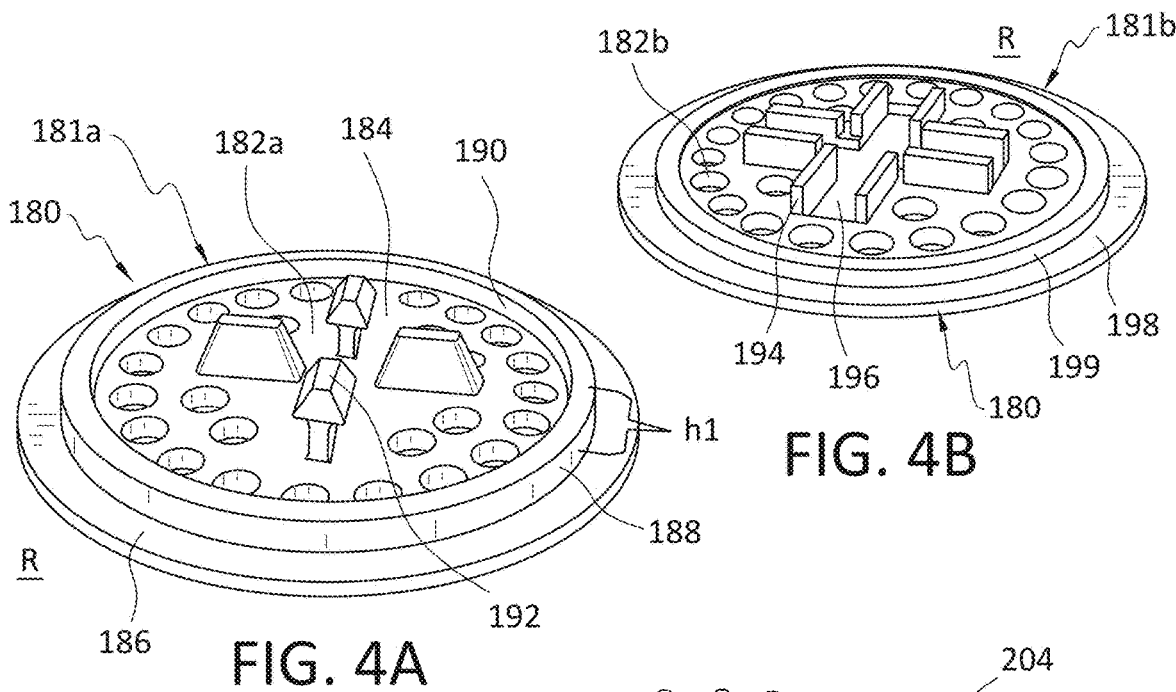
FIG. 4A
FIG. 4B
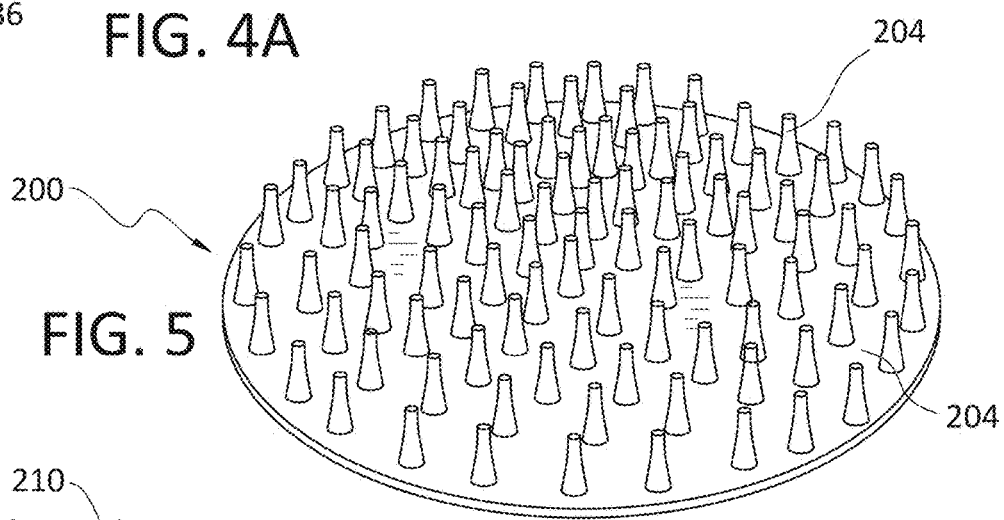
FIG. 5
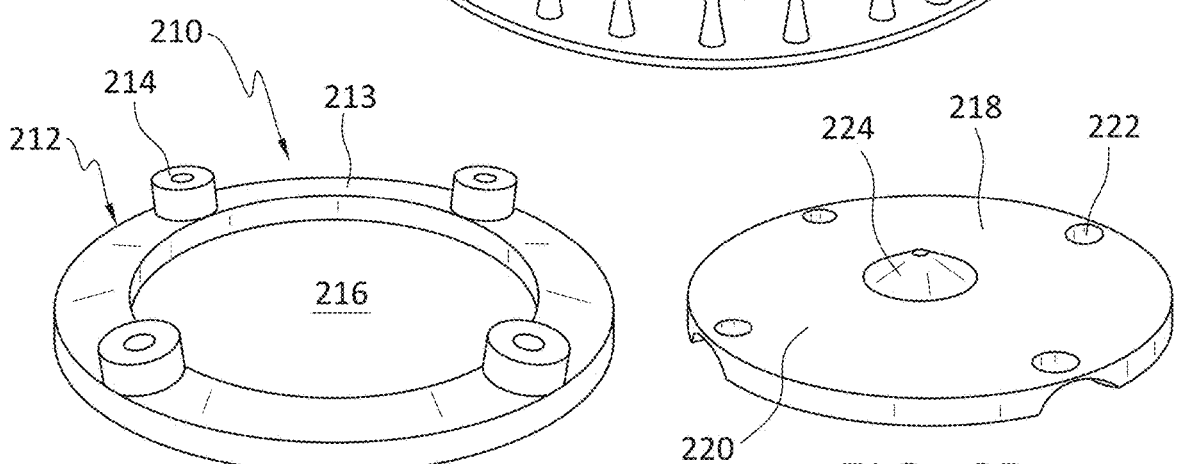
FIG. 6A
FIG. 6B

VENTILATED PROSTHETIC SOCKET AND KIT FOR MAKING THE SAME

FIELD OF THE DISCLOSURE

The disclosure relates to a ventilated prosthetic socket for use with a residual limb and corresponding prosthesis system. The ventilated prosthetic socket may include discretely formed vent elements disposed about a circumference of the ventilated socket, and a method and kit are provided for making such ventilated prosthetic socket.

BACKGROUND

A prosthetic socket is part of a prosthesis system that conforms to a residual limb. The prosthetic socket serves as an interface between the residual limb and a prosthesis. The prosthetic socket protects the residual limb, and, in the event of a lower limb prosthesis system, the prosthetic socket is sufficiently structured to transmit forces associated with standing and walking and handle stresses associated with weight-bearing, suspension, and ambulation. An example of a prosthetic socket is disclosed in at least U.S. Pat. No. 5,718,925, granted Feb. 17, 1998, and U.S. Pat. No. 7,438,843, granted Oct. 21, 2008, each document incorporated herein by reference.

The prosthetic socket must properly conform to the residual limb and make the prosthetic foot and/or knee work. As residual limbs are often irregular and comprise tender tissue, the prosthetic socket will often determine the quality and duration an amputee can function in the prosthesis system. In addition, the prosthetic socket can dictate the efficacy of gait performance with the prosthesis system by an intimate and comfortable fit. Regardless of the advancement of a prosthesis system, if the prosthetic socket fits poorly and is uncomfortable, the other components of the prosthesis system may be negated.

A prosthetic socket may be donned with a suspension liner as an interface between the socket and the residual limb. An example of a suspension liner is described in at least U.S. Pat. No. 6,416,703, granted Jul. 9, 2002, U.S. Pat. No. 10,342,682, granted Jul. 9, 2019, U.S. Pat. No. 10,420,657, granted on Sep. 24, 2019, and U.S. Pat. No. 10,729,566, granted on Aug. 4, 2020, each document incorporated herein by reference. The suspension liner spreads pressure across the residual limb surface at a comfortable level to the amputee. In addition, the suspension liner may be provided with means to provide vacuum suspension to the prosthetic socket, thereby creating a seal between the residual limb and the prosthetic socket.

As each residual limb is unique, prosthetic sockets may likewise be fabricated to the unique contours of an individual residual limb. Nonetheless, certain qualities are shown to enhance comfort and functionality. A prosthetic socket often provides total contact with the residual limb. This means that the prosthetic socket fully embraces and encircles the residual limb. Even when donned with a suspension liner as an interface between the residual limb, an interior surface of the prosthetic socket is preferably contoured to the shape of the residual limb.

Some materials used for constructing prosthetic sockets are flexible to adapt to the body and absorb the energy generated during the gait cycle or rigid to control the bending generated by the loads. Similarly, prosthetic sockets must be safe and durable and have sufficient strength to withstand the maximum stresses expected from being subjected to normal pressure by the action of weight and gait, which generate tensile and compressive stress, in addition to tangential stress that occurs when prosthetic sockets and the affected limbs interact. Prosthetic sockets and interfaces must allow for the damping of the stresses generated and adequate adjustment to correctly transfer the pressures when using them, considering each patient's clinical requirements.

Prosthetic liners made of solid elastomers like silicone, copolymer gel, or polyurethane have been commercially available and used for some years as the media next to the skin in the majority of lower extremity prostheses.

Such liners have solved many issues like friction and pressure distribution; however, it has been difficult to achieve effective heat and sweat management when using a non-porous interface. For instance, moisture, e.g., sweat or condensation within the liner, can adversely affect limb health. Moisture decreases the friction suspending the liner on the residual limb. This can cause a pistoning action, which describes the relative movement between the liner and the residual limb.

Excessive limb pistoning tends to lead to friction-related injuries such as friction blisters and skin irritation. It also creates the potential for catastrophic failure of the suspension of the limb. Problems such as dermatitis and infection are also common, particularly if the liner and residual limb are not cleaned appropriately or frequently.

Attempts have been made to remove heat and sweat using different liner type suction interfaces, yet, such interfaces are relatively complex, short-lasting, ineffective, uncomfortable, and inevitably prohibit their use with a large majority of users more effectively. For instance, one approach applies an elevated vacuum to draw sweat across the proximal edge of a prosthetic liner. However, sweat accumulates at the bottom of a liner, and an elevated vacuum does not reverse that. Further, the elevated vacuum tends to seal inside the liner and the proximal edge, preventing the removal of the sweat. An elevated vacuum applied to the liner's proximal edge tends to cause blisters, making the liner extremely uncomfortable.

Recently, improved liners concerning moisture control have been designed to offer ventilation; however, sockets have yet to be designed to accommodate such ventilated liners. Examples of such liners are offered in U.S. patent application publication no. 2020/0146850, published on May 14, 2020, incorporated herein by reference, and U.S. Pat. No. 10,729,566. Indeed, these improved liners manage perspiration formed by a limb, prevent slippage of the liner, and provide suitable cushioning for the limb. Such a liner can be used in various applications for both prosthetic and orthopedic systems in combination with prosthetic and orthopedic devices.

Nonetheless, given the total contact nature and rigidity of many known prosthetic socket designs, these known prosthetic sockets lack the means to vent the moisture and air permitted by the liner through a thickness of the socket. Accordingly, there is a need for a prosthetic socket that can accommodate the ventilation of a liner and permit a transfer of air through the prosthetic socket, thereby providing a ventilated prosthesis system.

SUMMARY

The disclosure describes various embodiments of a ventilated prosthetic socket, methods, and a kit for making the same. The embodiments offer simple, comfortable, and effective ventilation and heat management without the bulk and complexity of conventional heat management elements in known prosthetic socket systems. The embodiments can manage the build-up of sweat in a liner with heat management features that are easily and conveniently maintained, adjusted, and/or controlled without having to remove components from a user's prosthetic socket system.

The embodiments described include a prosthetic system with a prosthetic socket with an inner surface defining a socket cavity. A liner is adapted to receive a residual limb therein and be removably positioned within the socket cavity. A substantially sealed volume may be defined between at least a portion of the outer surface of the liner and a corresponding portion of the inner surface of the socket. A ventilation management system is provided and incorporated with the socket to vent air and moisture from an interior volume of the prosthetic socket and through a wall thickness from an interior surface to an exterior surface of the prosthetic socket.

The ventilation management systems are provided and may be used to form the prosthetic socket, and may be permanently provided therewith. The ventilation management systems include individual vents that may be selectively located along with a height of a socket relative to an axis of the prosthetic socket or provided as a plurality of vent elements arranged in a strip for inclusion in a socket as a unit. Vent elements may be provided that comprise parts that can interconnect for installation in a prosthetic socket.

These and other present disclosure features will become better understood regarding the following description, appended claims, and accompanying drawings.

BRIEF DESCRIPTION OF THE DRAWINGS

FIGS. 2A-2D are plan views of variations of vent elements for use in the prosthetic socket of FIG. 1 and useable in a kit for making the prosthetic socket of FIG. 1.

FIGS. 3A and 3B are perspective views of a variation of the vent element assembly in FIG. 1D.

FIGS. 4A and 4B are perspective views of a variation of a vent assembly.

FIG. 5 is a perspective view of a vent template for creating a vented structure in a prosthetic socket.

FIGS. 6A and 6B are perspective views of a variation of a vent template or variation of a vent element.

Figure 1A:
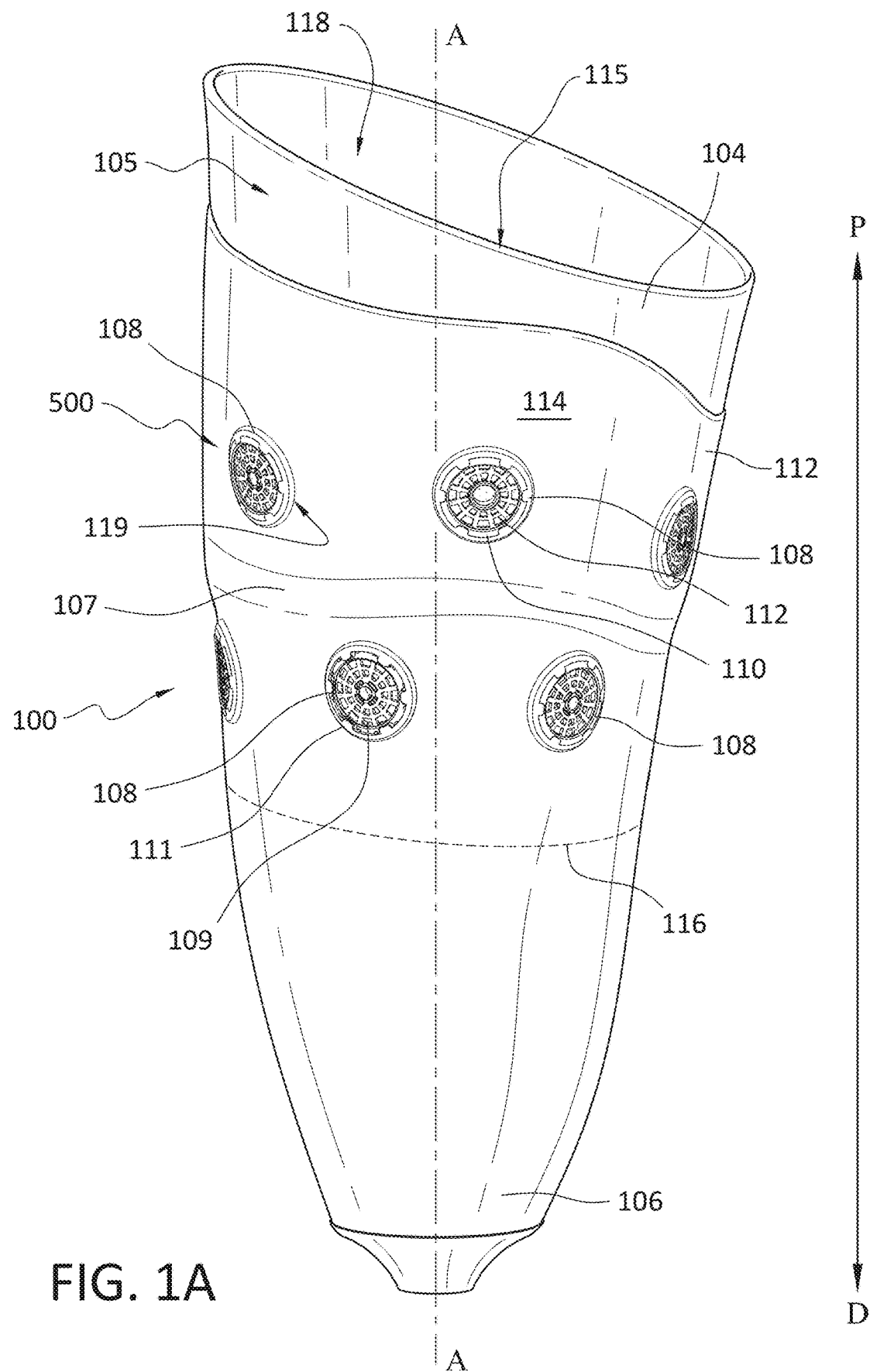
FIG. 1A is a perspective view of an embodiment of a ventilated prosthetic socket.

The drawing figures are not necessarily drawn to scale. Instead, they are drawn to understand better the components and are not intended to be limited in scope but to provide exemplary illustrations. According to the present disclosure, the figures illustrate exemplary configurations of a prosthetic socket and features for a kit in making a prosthetic socket with ventilated features.

DETAILED DESCRIPTION

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings described below. It should be understood, however, there is no intention to limit the disclosure to the specific embodiments disclosed, but on the contrary, the intention covers all modifications, alternative constructions, combinations, and equivalents falling within the spirit and scope of the disclosure.

For further ease of understanding the embodiments of an orthopedic device as disclosed herein, a description of a few terms is necessary. As used herein, the term "proximal" has its ordinary meaning and refers to a closer location to the heart than another location. Likewise, the term "distal" has its ordinary meaning and refers to a further location from the heart than another location. The term "posterior" also has its ordinary meaning and refers to a location behind or at another location's rear. Lastly, the term "anterior" has its ordinary meaning and refers to a location ahead of or to the front of another location.

The terms "rigid," "flexible," and "resilient" may be used herein to distinguish characteristics of portions of certain features of the orthopedic device. The term "rigid" is intended to denote that an element of the device is generally devoid of flexibility. On the other hand, the term "flexible" is intended to denote that features are capable of repeated bending such that the features may be bent into retained shapes or the features do not retain a general shape but continuously deform when force is applied. The term "resilient" is used to qualify such flexible features as generally returning to an initial general shape without permanent deformation. As for the term "semi-rigid," this term is used to connote properties of elements that provide support and are free-standing; however, such elements may have some degree of flexibility or resiliency.

It will be understood that unless a term is expressly defined in this application to possess a described meaning, there is no intent to limit the meaning of such term, either expressly or indirectly, beyond its plain or ordinary meaning.

Any element in a claim that does not explicitly state "means for" performing a specified function, or "step for" performing a specific function is not to be interpreted as a "means" or "step" clause as specified in 35 U.S.C. § 112.

Referring to the embodiment of FIG. 1A, a prosthetic socket 100 comprises a rigid, structural, and load-bearing socket body 102 in the form of a closed-ended cup defining an open-ended proximal end area 104 and a closed-ended distal end area 106. The socket body 102 forms an inner volume 118 adapted to receive a residual limb. The socket body 102 defines a wall thickness t from an inner surface 113 bordering the inner volume 118 to an outer wall surface 114.

A flexible brim 105 is provided along the proximal end of the socket body 102, extending proximally past a peripheral edge 115 of the rigid prosthetic socket. An interior interface of the brim to the rigid prosthetic socket may be delineated on an exterior of the prosthetic socket 100 by a circumferential bulge 107. Examples of a brim are described in U.S. Pat. No. 9,474,635, granted on Oct. 25, 2016 and incorporated herein by reference.

At least one vent element 108 communicates the inner wall surface 113 to the outer surface 114 and extends therebetween along the socket body 102 to thereby permit a transfer of air from the inner volume 118 to outside of the prosthetic socket 100. The at least one vent element 108 includes a plurality of vent elements 108 to enable air and moisture transfer from the inner volume 118 to the ambient outside the prosthetic socket 100, thereby ventilating the prosthetic socket 100, unlike in known prosthetic sockets.

The vent element 108 spans the wall thickness between the inner surface 113 and the outer wall surface 114. The vent element 108 may be embedded in a rigid structural material forming the socket body 102, or may be provided as separate parts separate from the prosthetic socket 100. For example, as shown in at least FIGS. 4a and 4b, the vent element 180 may comprise at least two parts that are securable to one another, but that such parts may be removable to provide for changing the vent element 180 or a ventilation structure 182 of the vent element 180.

Figure 1B:
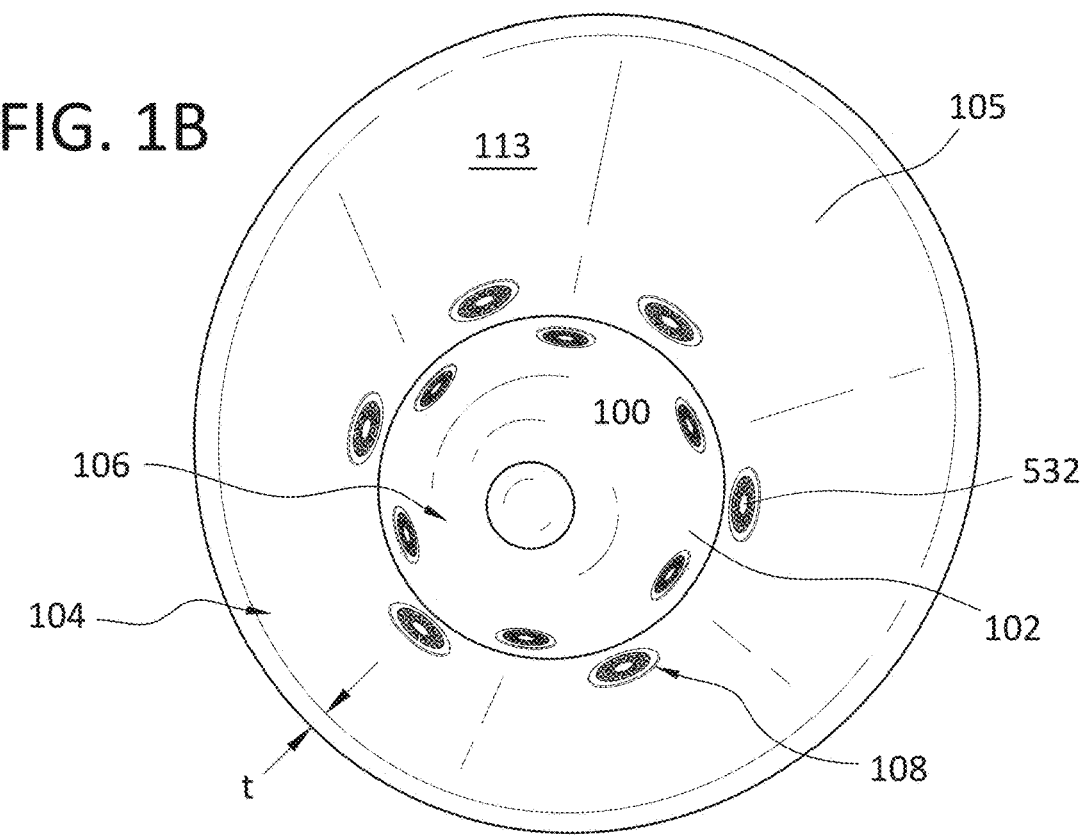
FIG. 1B is a plan view of an inner volume of the prosthetic socket in FIG. 1A.

As illustrated in FIGS. 1A and 1B, the at least one vent element 108 includes a plurality of vent elements 108 extending in a circumferential configuration about an axis A-A of the socket body 102. The at least one vent element 108 includes a first row of sequentially spaced individual vent elements 108 extending about a circumference of the socket body 102 about an axis A-A of the socket body 102. The at least one vent element 108 includes a second row of sequentially spaced individual vent elements 108 staggered circumferentially about the axis A-A relative to the first row of vent elements 108.

The at least one vent element 108 extends between the proximal end area 104 and the distal end area 106. For example, in the embodiment of FIGS. 1A and 1B, the at least one vent element 108 is located proximally above a seal region 116 extending circumferentially about the inner wall surface 113 distally of the at least one vent element 108.

The at least one vent element 108 includes a ventilated structure 112 permitting air transfer from the inner volume 118 to outside the socket body 102. The at least one vent element 108 may define a flanged rim 110 extending about a periphery thereof and about a segment of the outer wall surface 114 of the socket body 102. The flanged rim 110 preferably surrounds the ventilated structure 112. A mesh insert 109 may cover the ventilated structure 112 and be encapsulated by a rim 111 at least about a periphery of the mesh insert 109.

The ventilated structure 112 preferably defines a plurality of apertures communicating the inner volume 118 to the outside of the socket body 102. The size and density of apertures may vary from each vent element, be selected upon the desired amount of ventilation required or desired of the prosthetic socket, and may differ among other vent elements in a given prosthetic socket or strategic locations along the prosthetic socket wall.

The at least one vent element 108 defines inner and outer flanged rims 110, corresponding to the inner surface wall surface 113 and the outer wall surface 114, respectively. Alternatively, the at least one vent element 108 may include only one flanged rim 110 depending on one of the inner or outer wall surfaces 113, 114 or be devoid of any flanged rims 110. The socket body 102 may define an opening 119 extending through a thickness of the wall thickness t into which the vent element may be inserted, or the opening 119 may be formed about a vent element that is integrated with the prosthetic socket 100 during fabrication.

Figure 1C:
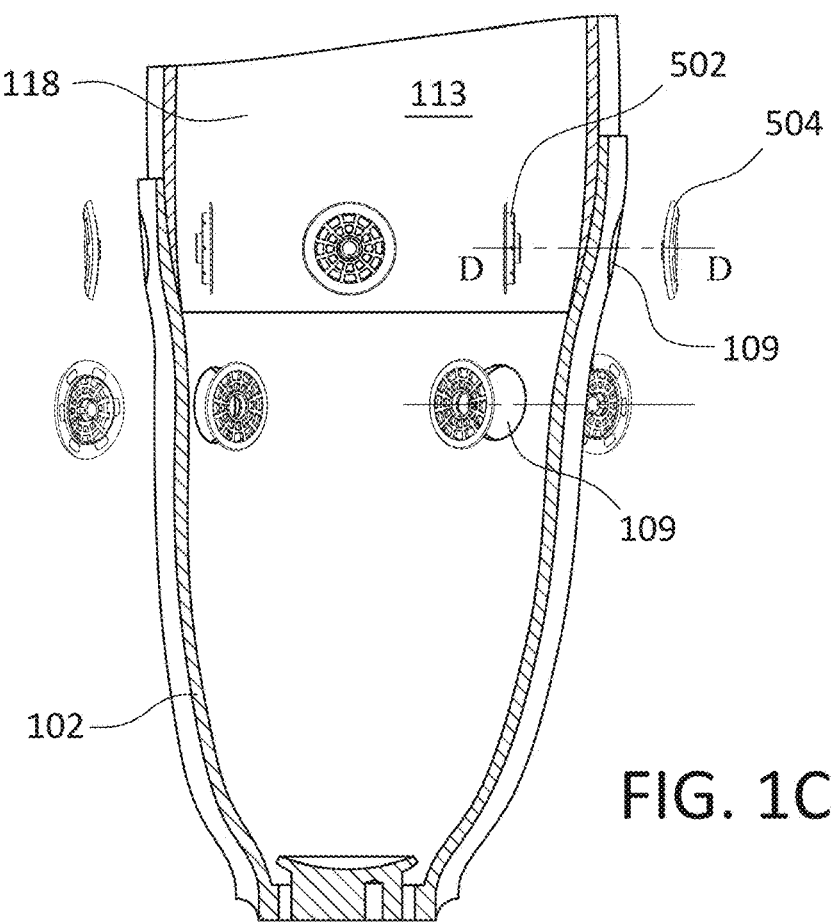
FIG. 1C is an exploded cross-sectional view of an embodiment of a vent assembly.

FIG. 1C illustrates an embodiment of how a vent element may be incorporated and assembled into the prosthetic socket 100. The interior part 502 is located within the inner volume 118 and the exterior part 504 is located on the exterior of the prosthetic socket 100, the interior and exterior parts 502, 504 being concentrically aligned with an opening 119 along an exemplary axis D-D such that they can be coupled together through the opening 119.

Figure 1D:
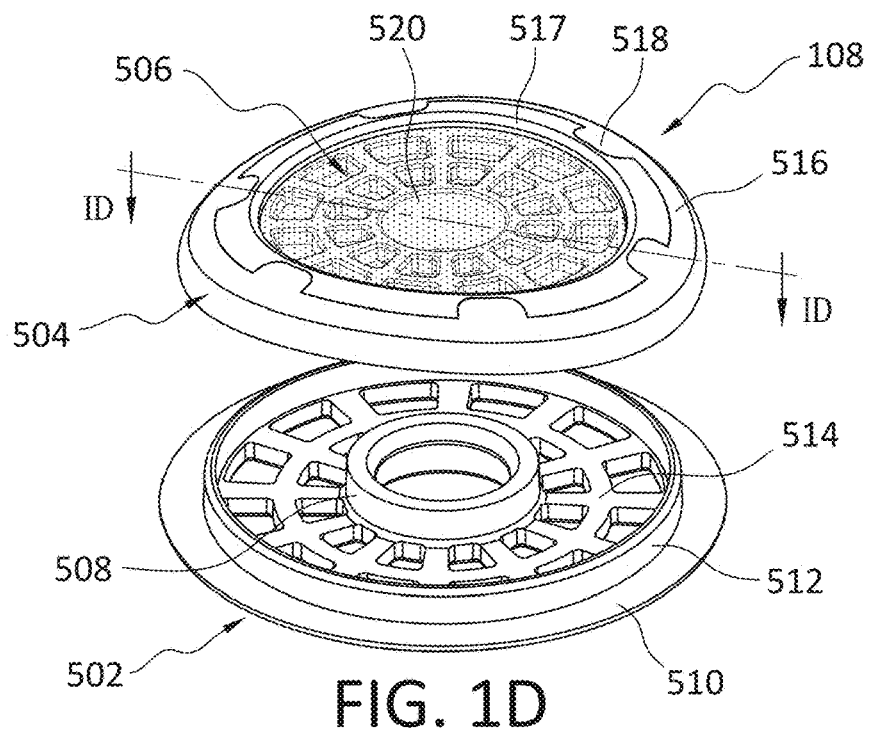
FIG. 1D is an exploded view of an embodiment of a vent assembly.
Figure 1E:
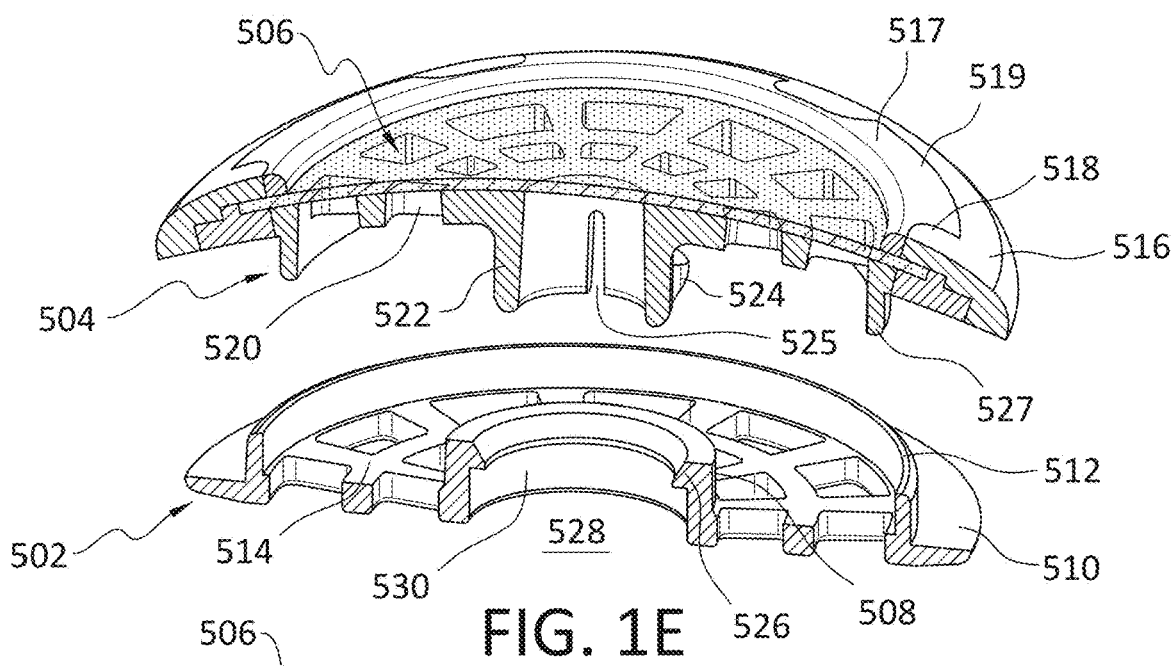
FIG. 1E is a cross-sectional view taken along line ID-ID in FIG. 1D.
Figure 1F:
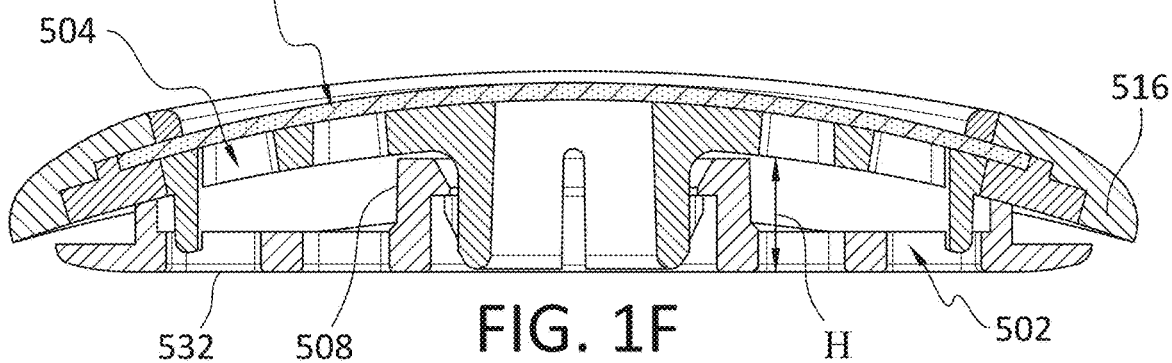
FIG. 1F is a cross-sectional view of the vent assembly in FIGS. 1D and 1E in an assembled configuration.

FIGS. 1D-1F illustrate an embodiment of a vent element 500 in FIG. 1A having a ventilated structure. The vent element 500 includes an interior or first part 502, an exterior or second part 504, and a mesh insert 506, such a textile or foam. The interior part 502, as illustrated schematically in FIG. 1F, has an interior surface 532 configured and dimensioned to be flush with the inner wall surface 113 in FIG. 1B. The mesh insert 506 and a rim 517 and flange tabs 518 extend over and secure the mesh insert 506 on the exterior side of the prosthetic socket 100. The flange tabs 518 of the exterior part 504 protrude inwardly toward the mesh insert 506 from a circumferential flange 516 that overlies the outer wall surface 114 of the prosthetic socket 100. The rim 517 may be formed from a separate material than the exterior part 504 and the mesh insert 506, and interlocks with the inner periphery 519 of the circumferential flange 516 and the flange tabs 518. The rim 517 may be formed from a more elastic material than the material forming the exterior part 504.

The exterior part 504 forms a ventilation structure 520 of a network or grid of structural elements including a plurality of interstices or voids permitting a transfer of air therethrough. The ventilation structure 520 is preferably rigid to underlie the mesh insert 506, and prevent and protect the inner volume 118 of the prosthetic socket 100 from the accumulation of debris or any other matter from the exterior of the prosthetic socket 100. The exterior part 504 forms a cylinder 522 arranged to be directed to the interior volume 118 and through the thickness t of the prosthetic socket wall. Indeed, as shown in FIG. 1F, the cylinder 522 may have a height H generally corresponding to the thickness t. The cylinder 522 may form a split 525 permitting a snap-fit into and about an opening 528 formed by a boss 508 defined by the interior part 502.

The cylinder 522 preferably defines a circumferential outer prong 524 that is arranged to engage an inner prong 526 formed by an inner surface of the boss 508, as exemplified by FIG. 1F. The outer prong 524, once fitted in the boss 508, rests in an opening recess 530 formed by the inner surface of the boss 508, below the inner prong 526.

Like the ventilated structure 520 of the exterior part 504, the interior part 502 forms a ventilated structure 514 having a grid-like structure and adapted to permit a flow of air from the interior of the prosthetic socket to the exterior of the prosthetic socket, yet protect the interior of the prosthetic socket from the exterior of the prosthetic socket. The interior part 502 has a circumferential flange 510 from which a rim 512 protrudes toward the exterior part 504, and is configured and dimensioned to extend snugly and flush with and about the opening 119. The exterior part 504 likewise forms a rim 527 extending toward the interior part 502, and fits circumferentially about and within the rim 512 of the interior part 502.

In a method for making the vent element, the exterior part 504 may be first formed, and then the mesh insert 506 is placed on top of the exterior part 504 within the exterior recess defined by the inner periphery 519 of the circumferential flange 516. The rim 517 may then be molded over or about the inner periphery 519. Interlocking features, such as openings, may be formed on the exterior part 504 about the inner periphery 519 in which material of forming the rim 117 may interlock. From this point, the mesh insert 506 is fully secured to the exterior part 504, and no further assembly is required.

Despite the depicted embodiment of FIGS. 1D-1F, how the interior and exterior parts 502, 504 secure and mount to one another can be selected from other known means for securing disks or circular elements. An objective to this embodiment is the provision of interior and exterior parts 502, 504 that secure one another to protect the openings of a prosthetic socket and permit a transfer of air to one another. The interior and exterior parts 502, 504 can be provided with or without the mesh insert 506. The ventilation structure can be formed according to configurations to permit the flow of air from the interior to the exterior of the prosthetic socket while protecting the interior of the prosthetic socket. The interior part 502 can be flush with the inner wall surface 113, as depicted in FIG. 1B, whereas the circumferential flange 516 of the exterior part 504 can radially extend past the opening 119 formed by the prosthetic socket into which the vent element is placed.

Figure 1G:
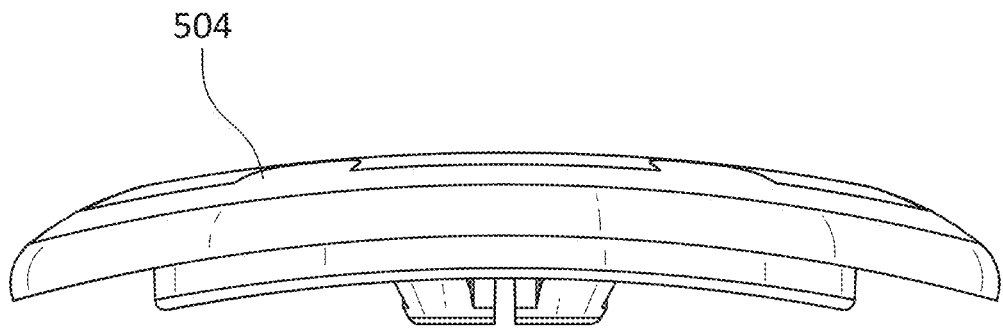
FIG. 1G is a front view of an exterior part of the vent assembly in FIGS. 1D and 1E.
Figure 1H:
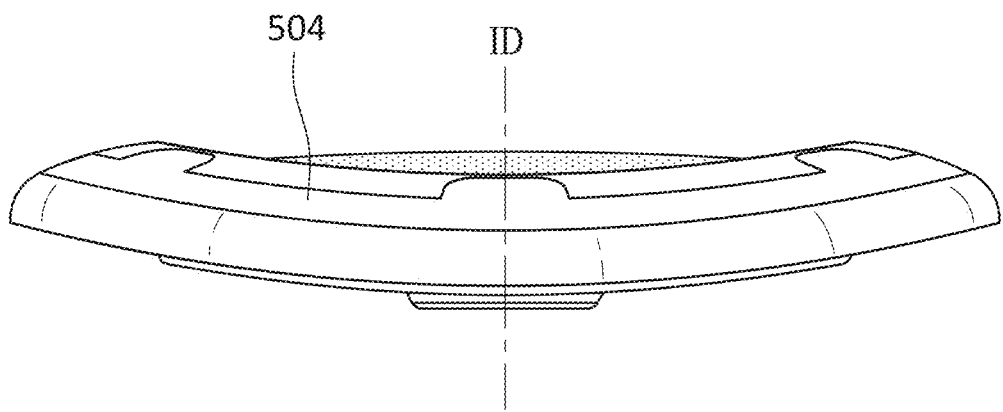
FIG. 1H is a side view of the exterior part of the vent assembly in FIG. 1G.

The exterior part 504 may have the geometric shape of a saddle, or hyperbolic paraboloid, as shown in FIGS. 1G and 1H such that the exterior part 504 closely tracks the geometric profile of the outer wall surface 114. The exterior part 504 should have a low profile and closely track the geometric profile of the outer wall surface 114 to prevent the prosthetic socket from getting caught on foreign objects what may come into contact with the prosthetic socket. As shown in FIGS. 1A, 1B, and 1C, the prosthetic socket 100 is cylindrical, terete, or cup shape, having a nearly circular horizontal cross section which fluctuates in diameter along the vertical axis.

Forming the exterior part 504 in a saddle shape, or hyperbolic paraboloid, allows the exterior part 504 to closely track the geometric shape of the outer wall surface 114. In particular, the surface of the exterior part 504 that couples with the interior part 502 may be concavely curved along the line ID shown in FIGS. 1D and 1G while being convexly curved along a line perpendicular to the line ID as shown in FIG. 1H. The concavely curved portion of the exterior part 504 may closely track the horizontal geometric cylindrical curvature of the outer wall surface 114 while the convexly curved portion of the exterior part 504 may closely track the vertical geometric shape of the outer wall surface 114 thus resulting in a low profile in which exterior part 504 "wraps" around a segment of the outer wall surface 114.

As illustrated in at least FIG. 2A, the vent element 120 preferably defines a ventilation structure 122 centrally located about an axis X of the vent element 120. The vent element 120 generally defines a circular profile about the axis X of the vent element. The vent element 120 may have a profile selected from various shapes, including circles, squares, or other suitable shapes to conform to the prosthetic socket body. The vent elements of a prosthetic socket may vary in shape and size relative to one another depending on their location along the prosthetic socket axis A-A or strategic areas for ventilating the prosthetic socket.

The vent element 120, preferably, defines central section 124 protruding from a rim section 126. The central section 124 extends along the axis X. The rim section 126 extends radially relative to the axis X, and the central section 124 generally protrudes a distance 128 from the rim section 126 at about the wall thickness t. The central section 124 is correspondingly sized to fit within the opening 119, thereby being snugly maintained within the wall thickness t.

The central section 124 may be arranged to protrude toward the inner wall surface 113. The rim section 126 may be adapted to be arranged along the outer wall surface 114 of the prosthetic socket 100, extending over the outer wall surface 114 or within a recess corresponding in size to the rim section 126 so the rim section 126 is flush with the outer wall surface 114. This arrangement may mitigate the vent element 120 from protruding from the outer wall surface 114.

As shown in FIGS. 2A-2D, the ventilation structure 132, 142, 152 of vent elements 120, 130, 140, and 150 may be selected from a plurality of shapes and sizes of apertures.

According to FIGS. 3*a* and 3*b*, the vent element 160 forms a ventilation structure 162 defined within a central section 164. The central section 164 is recessed with a central recess 168 relative to a rim section 166. The central recess 168 is arranged to receive a textile insert 170 when concentrically aligned along axis Y-Y.

The textile insert 170 has an outer periphery 172 corresponding in shape to the central section 164, and a thickness in which the textile insert 170 is flush with the rim section 166. The textile insert 170 has a ventilated structure comprising a plurality of apertures smaller than a plurality of apertures of the ventilated feature 162 of the central section 164.

FIGS. 4A and 4B depict a multiple part vent element 180. The vent element 180 defines a first part 181*a* having a first ventilation structure 182*a* and a second part 181*b* having a second ventilation structure 182*b*. The first and second parts 181*a*, 181*b* have first and second interlocking features 192, 194, respectively, arranged to couple the first and second parts 181*a*, 181*b* together. The first and second interlocking features 192, 194 provide a snap connection wherein the first interlocking feature 192 is inserted into the socket 196, thereby preventing separation of the first and second parts 181*a*, 181*b*.

The first part 181*a* defines a central section 184 and a rim section 186. The first part 181*a* includes a ring portion 188 extending perpendicularly relative to the rim section 186 and divides the central section 184 from the rim section 186. The second part 181*b* includes a raised portion 199 protruding therefrom and is arranged to correspond to an inner diameter 190 of the rim section 186 for snugly fitting the first part 181*a* to the second part 181*b*. The first interlocking feature 192 may define a plug arrangement adapted to fit within a socket arrangement defined by the second interlocking feature 194. The rim section 186 is arranged in size to correspond to a rim section 198 formed by the second part 181*b*. When the first and second parts 181*a*, 18*b* are coupled together, they are spaced apart by the height h1 of the rim section 186 such that the height h1 of the rim section 186 generally corresponds to a wall thickness t of the socket body 102 or a thickness between recessed sections of the socket body 102.

Figure 4C:
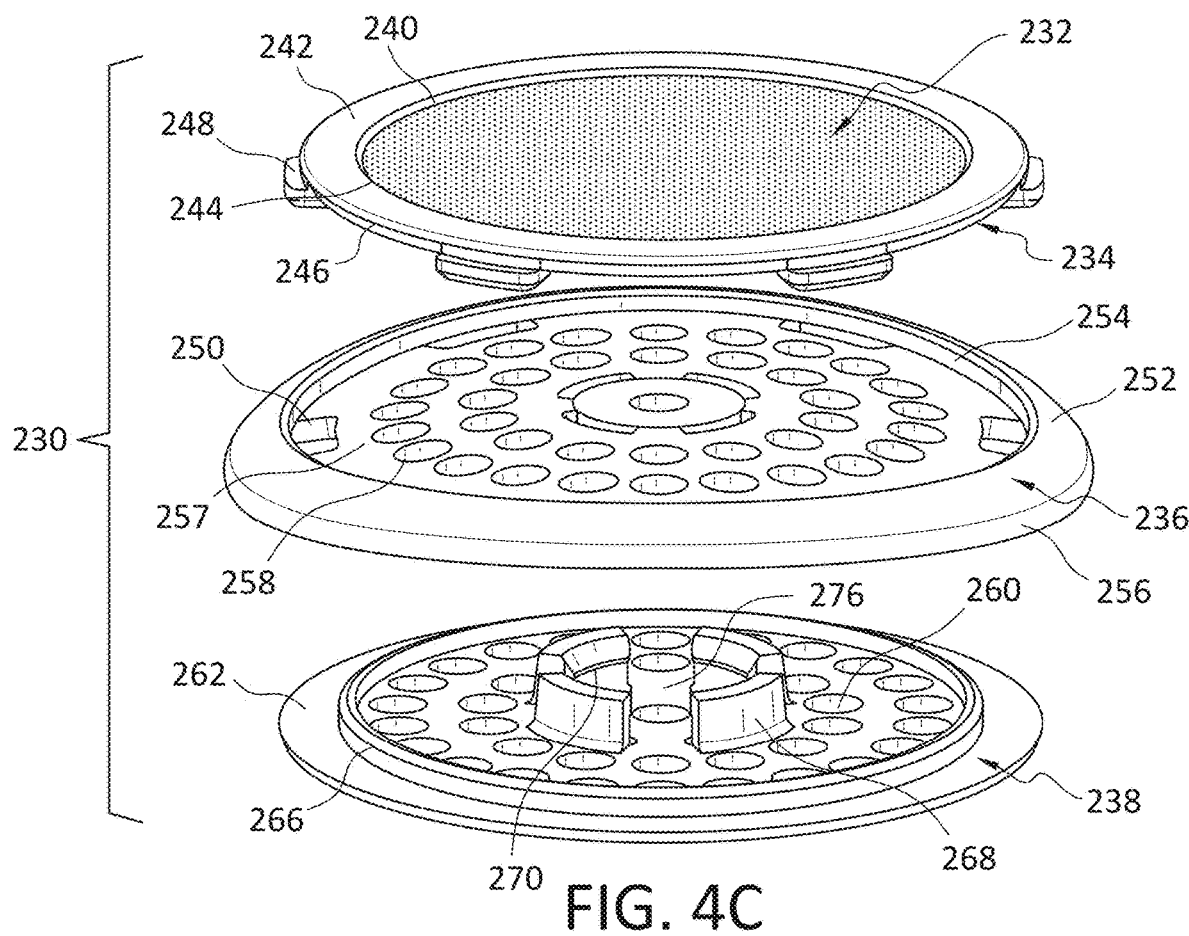
FIGS. 4C and 4D are exploded views of a variation of a vent assembly.
Figure 4D:
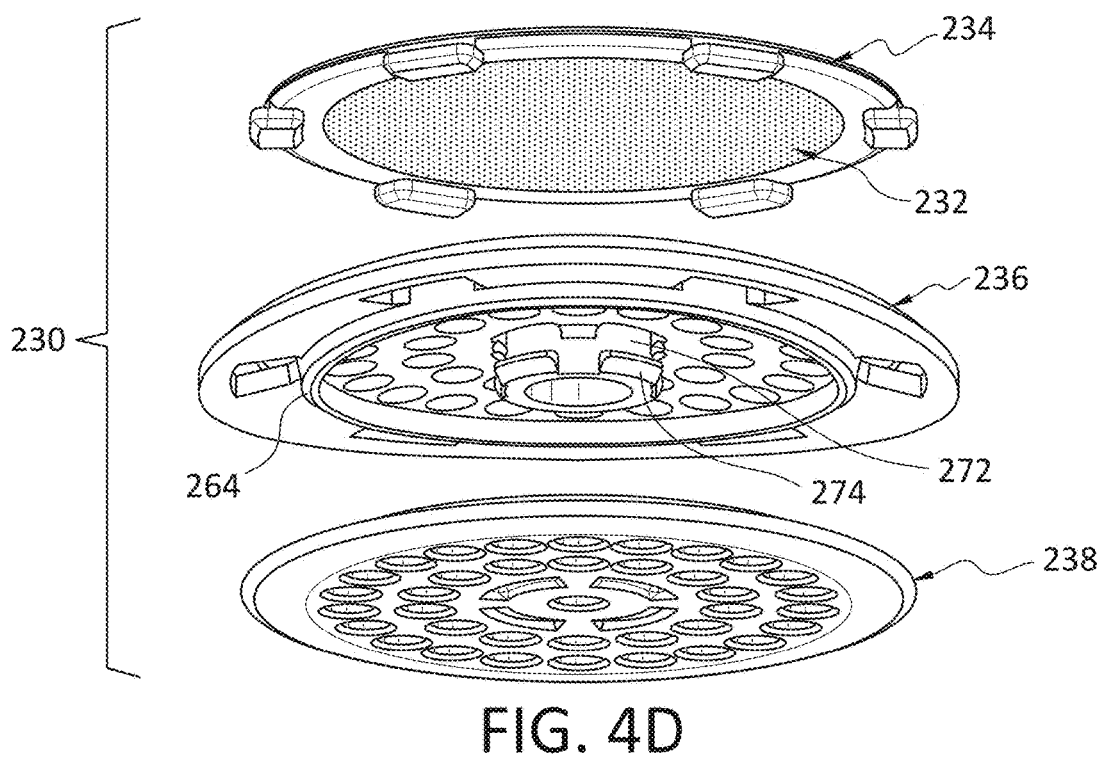

FIGS. 4C and 4D illustrate another vent element having an assembly 230. The assembly 230 includes a vent insert 232, an insert retainer 234, a first part 236 and a second part 238. The assembly 230 may be provided as a kit for forming a prosthetic socket and useable with templates described herein for forming openings in a prosthetic socket during fabrication.

The vent insert 232 may comprise a textile, foam, or other ventilated material. The vent insert 232 can be replaceable and has a periphery 240 that is insertable into the insert retainer 234. The vent insert 232 is preferably pliable to be insertable but retained by the insert retainer 234. The insert retainer 234 includes in a ring 242 having an inner periphery 244 adapted to retain the vent insert 232. Alternatively, the vent insert 232 may be adhered to the ring 242. An outer periphery 246 of the ring 242 defines at least one locking tab 248 for engaging with the first part 236 with a corresponding at least one tab locking part 250.

The insert retainer 234 is adapted to be received by a center portion 257 of a first side of the first part 236, and the first part 236 is preferably adapted to be arranged along an outer surface of the prosthetic socket. The first part 236 defines a rim 252 having an inner periphery 254 into which the insert retainer 234 may be secured, preferably in a snug, tight-fitting arrangement with the at least one locking tab 248 interlocking with the at least one tab locking part 250. The center portion 257 defines a ventilation structure 258 corresponding to the vent insert 238. The first side of the center portion 257 may be recessed along the inner periphery 254 so the insert retainer 234 is flush with the first side of the first part 236. An outer periphery 256 of the first part 236 is adapted to extend over the prosthetic socket's outer wall surface 114 or flush with a recess of the prosthetic socket's outer wall surface 114.

The first part 236 defines a locking cylinder 272 extending from a second side of the first part 236 opposite the first side. The locking cylinder 272 has an outwardly extending locking part 274 engageable with a corresponding fastener 270 extending along an internal surface of a boss 268 in an opening 276 thereof arranged to receive the locking cylinder 272. The boss 268 protrudes from the second part 238. Of course, while exemplary fasteners 270, 274 are illustrated, other suitable means or structure for fastening the first and second parts are envisioned, as would be foreseeable to one having ordinary skill in the art.

The first part 236 forms a first protruding section 264, such as a ring, extending from the second side of the first part 236, and corresponds to a corresponding second protruding section 266 formed by the second part 238 along a first side thereof. The first and second protruding sections 264, 266 are configured and dimensioned to interlock with one another to lock the first and second parts 236, 238 further. The second part 238 is adapted to be secured along the inner surface of the prosthetic socket 100. The height of the locking cylinder 272 and the boss 268, when the first and second parts 236, 238 are secured and locked to one another, should correspond to a wall thickness of the prosthetic socket to assure that the first and second parts 236, 238 secure to the socket wall, whether or not sunk into recesses formed by the outer and inner socket walls, or along the surfaces of the outer and inner socket walls, or any other suitable configuration. Additionally, the second part 238 has flange 262 located around the periphery of the protruding section 266, and a ventilation structure 260 located within the interior section of the protruding section 266.

According to FIG. 5, a vent template 200 comprising a plurality of protrusions 204 may be adapted to extend at least a thickness t of a socket body wall to impart a ventilated structure from a material or composite used to form the socket. The protrusions 204 extend from a plate 202 and may have various shapes, including conical, straight, etc. For example, at least one template may be strategically located during a socket formation along with a socket in fabrication to offer a ventilated region. The material forming the socket will form the socket about the protrusions, and the ventilated structure will be imparted into the socket. As in any other embodiments of the vent templates, they may be provided as a kit with means for fabricating a prosthetic socket.

Referring to FIGS. 6A and 6B, another vent template or vent element 210, comprises a first part 212 and a second part 218 that connect permanently with adhesive or interlocking parts or detachably connected by fasteners. The first and second parts 212, 218 have corresponding shapes and are adapted to be secured to one another. The first part 212 may be located along the inner wall surface 113 of the prosthetic socket, and the second part 218 is located along an outer wall surface 114 of the prosthetic socket.

The first part 212 forms a central opening 216 arranged to open to the inner volume 118 of the prosthetic socket. The first part 212 includes a ring 213 including at least one spacer 214 protruding therefrom and adapted generally to a wall thickness t of the socket body. The second part 218 has at least one connection 222, corresponding to the at least one spacer 214 to secure to the first part 212.

The at least one spacer 214 and the at least one connection 222 may be secured to one another by a fastener. The second part 218 may form a plate 220 adapted to include a valve 224 permitting a one-way passage of air from the inner volume 118 to outside the outer wall surface of the prosthetic socket. Alternatively, the second part 218 may form a ventilated structure as in any of the embodiments described and illustrated herein.

During fabrication, as in the embodiment of the vent template 200, at least one vent element 210 may be used during fabrication, and the vent template will impart an opening into which a vent element can be installed. The ring 213 may impart a recessed area along one of the inner or outer wall surfaces of the prosthetic socket. Once the socket is formed, the vent element 210 can be removed, thereby imparting an opening for receiving any vent element.

Figure 7:
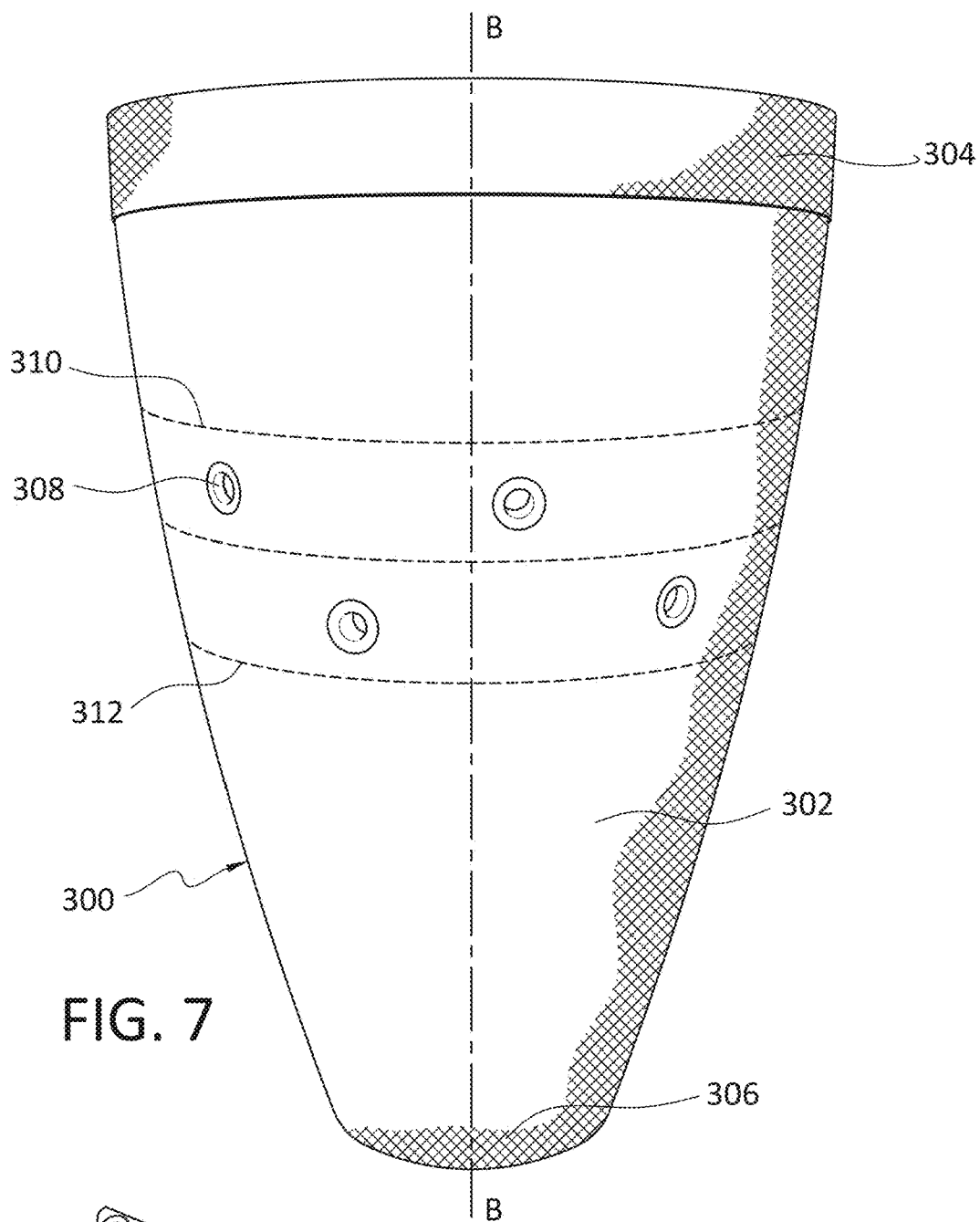
FIG. 7 is a perspective view of another embodiment of a ventilated prosthetic socket.

FIG. 7 illustrates an exemplary prosthetic socket 300 having a rigid, structural, and load-bearing socket body 302 in the form of a closed-ended cup defining an open-ended proximal end area 304 and a closed-end distal end area 306, as in the embodiment of FIG. 1. The socket body 302 forms an inner volume adapted to receive a residual limb, and the socket body 302 defines a wall thickness t from an inner surface bordering the inner volume to an outer surface.

At least one vent element 308 communicates the inner surface to the outer surface and extends therebetween along the socket body 302 to thereby permit a transfer of air from the inner volume to the outside of the socket.

The at least one vent element 308 comprises at least one array of vent elements 308 provided on at least one band or series of vent elements 310, 312 extending circumferentially about or within a thickness of the socket body 302. The first and second series of vent elements 310, 312 are axially spaced and located at first and second axial locations, respectively, relative to an axis B-B. The series of vent elements 310, 312 may be formed from an interconnected band of silicone or another type of pliable material, or separately formed.

Figure 8:
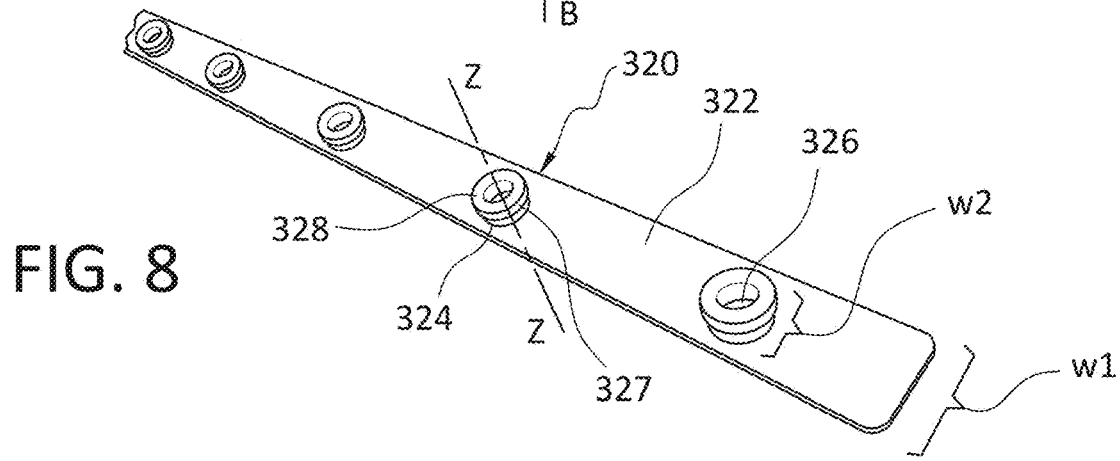
FIG. 8 is a perspective view of a band of vent elements or template for use in or fabrication of the prosthetic socket of FIG. 7 and useable in a kit for making the prosthetic socket of FIG. 7.

Referring to FIG. 8, a template band 320 may have at least one vent template 308. The template band 320 forms an elongate strip 322 along which a plurality of uniformly spaced vent elements 324 extend a distance or have a protruding section 327 protruding from the elongated strip 322. Each of the vent elements 324 of the plurality of uniformly spaced vent elements 324 may include a rim 328 adapted to form a recess along a wall surface of the socket body 302. Each vent element 324 may include an opening 326 extending entirely through the template band 320 and the protruding section 327. The opening 326 may be sized and configured to shape corresponding to a vent element installed in openings formed in the definitive socket with the template band. Alternatively, the template band 320 may be provided in the prosthetic socket, such that the template band 320 is adapted to be embedded within at least one structural layer forming the socket body.

The rim 328 corresponds to either the inner surface or the socket body's outer surface. In the alternative, each vent element 324 includes first and second rims extending about the first and second ends of the opening, thereby corresponding to both the inner outer surfaces. Alternatively, the vent element 324 is devoid of a rim, such that the protruding section extends from one of the inner or outer surfaces to another one of the inner or outer surfaces of the prosthetic socket.

As shown, the elongated strip 322 extends from one side of the vent element 324, and the protruding section 327 of the vent protrudes therefrom. Alternatively, the elongated strip 322 may be located at the height of the protruding section 327, opposed first and second sides of the vent element 324 extending axially beyond the band.

The rim 328 extends radially and parallel to the elongated strip, although the elongated strip may be flexible and bendable according to the contours of the prosthetic socket, and the shape of a residual limb. The protruding section of the vent element 324 preferably extends coaxially to an axis Z-Z of the vent element, and the elongated strip extends perpendicularly relative to the axis of the vent element.

The elongated strip 322 may have a greater width w1 than a diameter or width w2 of the vent element 324. The elongated strip 322 may provide greater surface area than a respective vent to enable secure adherence to the socket body and distribute pressure about the socket body 302.

Figure 9A:
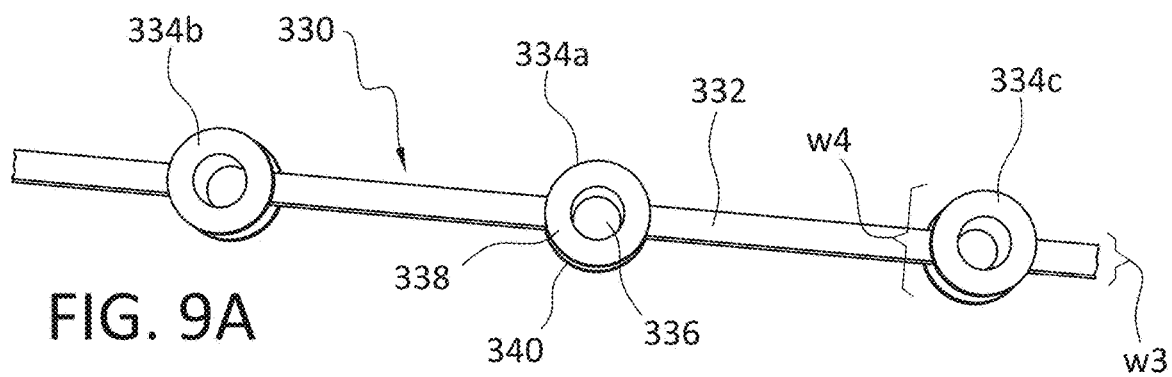
FIGS. 9A and 9B are perspective views of a variation of a band of vent elements for use in or a template in the fabrication of the prosthetic socket of FIG. 10 and useable in a kit for making the prosthetic socket of FIG. 10.
Figure 9B:
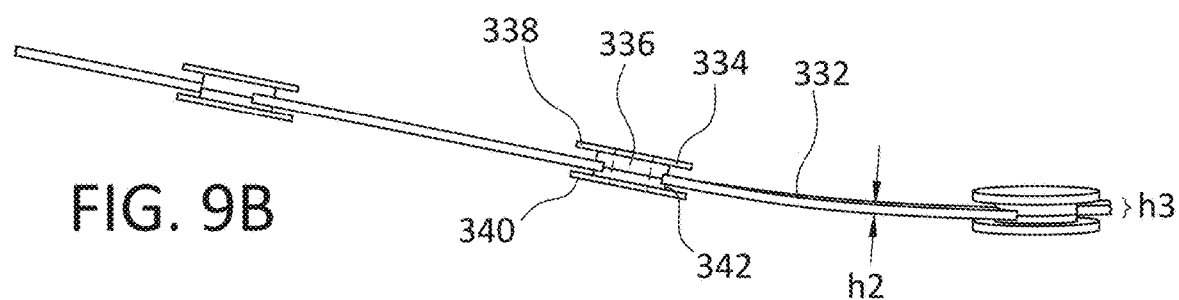
Figure 10:
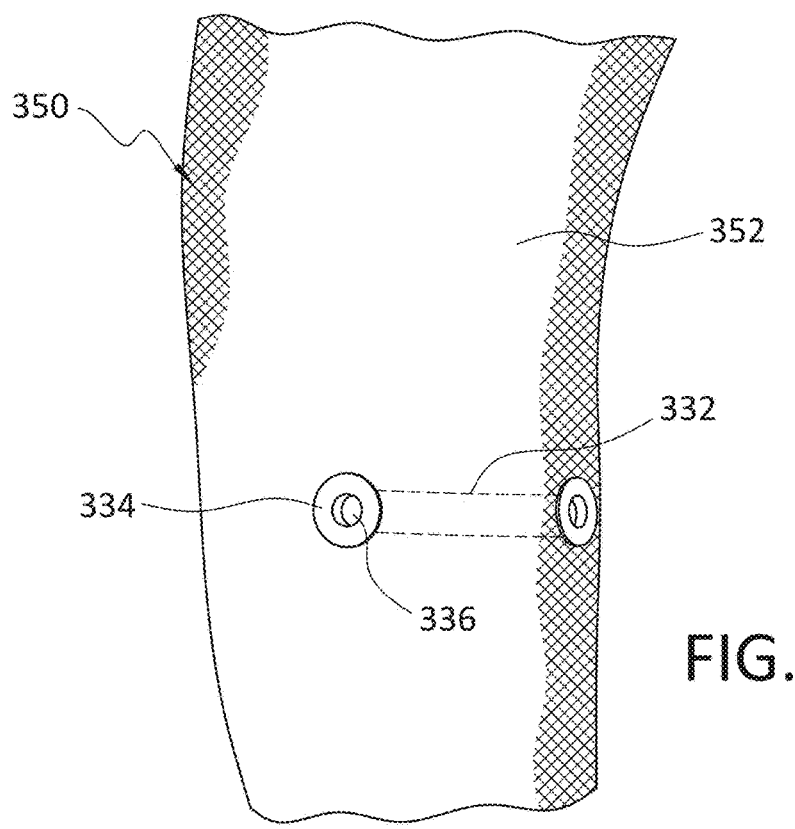
FIG. 10 is a perspective view of another embodiment of a ventilated prosthetic socket, including the vent elements or formed with a vent template of FIGS. 9a and 9b.

FIGS. 9A-10 exemplify another embodiment of a vent element or template for forming openings in a socket for receiving a vent element. A band 330 has at least two vent elements 334a, 334b, 334c connected by a strip 332. Each of the vent elements 334 has opposed sides defined by first and second rims 338, 340. The vent element 334 has a height 342, extending between the first and second rims 338, 340. The strip 332 extends between the first and second rims 338, 340 along with the height 342. The vent element 334 has a central opening 336 extending through an entirety of the vent element 334, including the first and second rims 338, 340. The strip 332 has a narrower width w3 than a width or diameter w4 of the vent element 334. The strip 332 has a narrower height or thickness h2 than a height h3 of the vent element 334 defined between the first and second rims 338, 340.

Similar to aforementioned templates, the band 330 may be used only during socket fabrication to impart a series of openings in a predetermined manner corresponding to the shape and spacing of the vent elements or templates 334a, 334b, 334c.

As illustrated by FIG. 10, the strip 332 may be arranged to be embedded within a thickness of the socket body. The at least one rim 338, 340 extends about or in a recessed section 354 of the inner or outer wall surface 352, as shown in the prosthetic socket 350. Alternatively, FIG. 10 may be interpreted to show openings formed by the vent templates.

Figure 11:
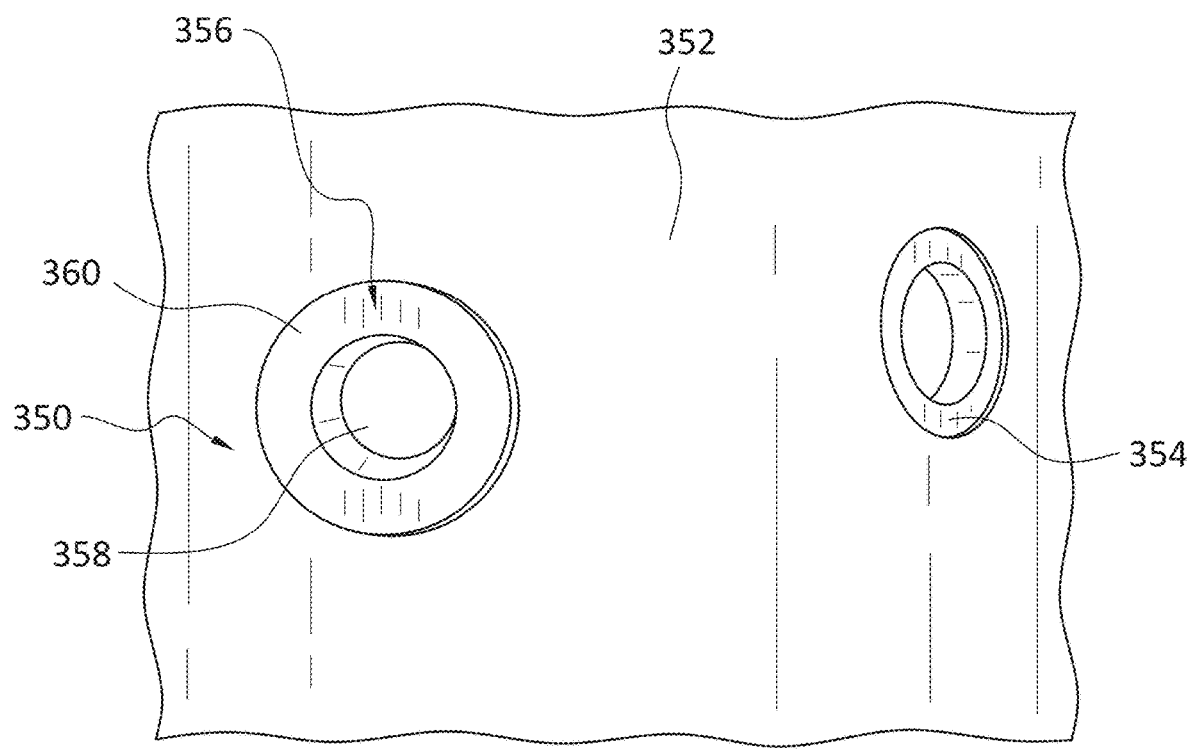
FIG. 11 is a schematic sectional view showing a socket wall in a ventilated prosthetic socket having sections formed with a vent template.
Figure 11A:
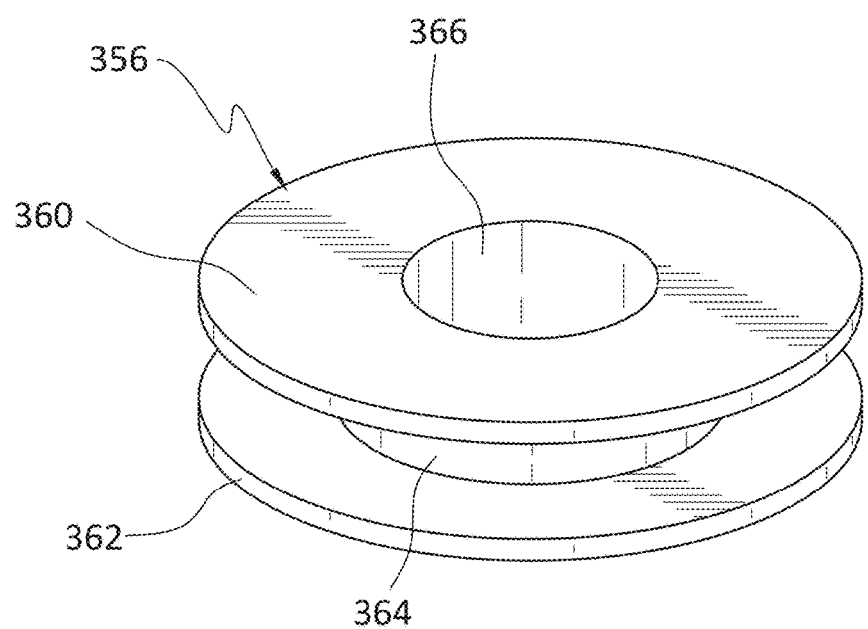
FIG. 11a is a schematic view of a vent element in the socket wall of FIG. 11.

FIG. 11 illustrates a socket wall 350 having a wall surface 352, with a recessed section 354 formed from vent template, such as those described above. The socket wall 350 forms an opening 358 formed by the vent template. FIG. 11a illustrates a vent element 356 forming a grommet that can be inserted through an entire wall thickness of the socket wall 350. The vent element 356 forms first and second flanges 360, 362 arranged for opposed sides of the inner and outer wall surfaces. The vent element 356 forms a central opening 366 intended coaxial to the opening 358 of the socket wall 350 with a standoff 364 separating the first and second flanges 360, 362.

Figure 12:
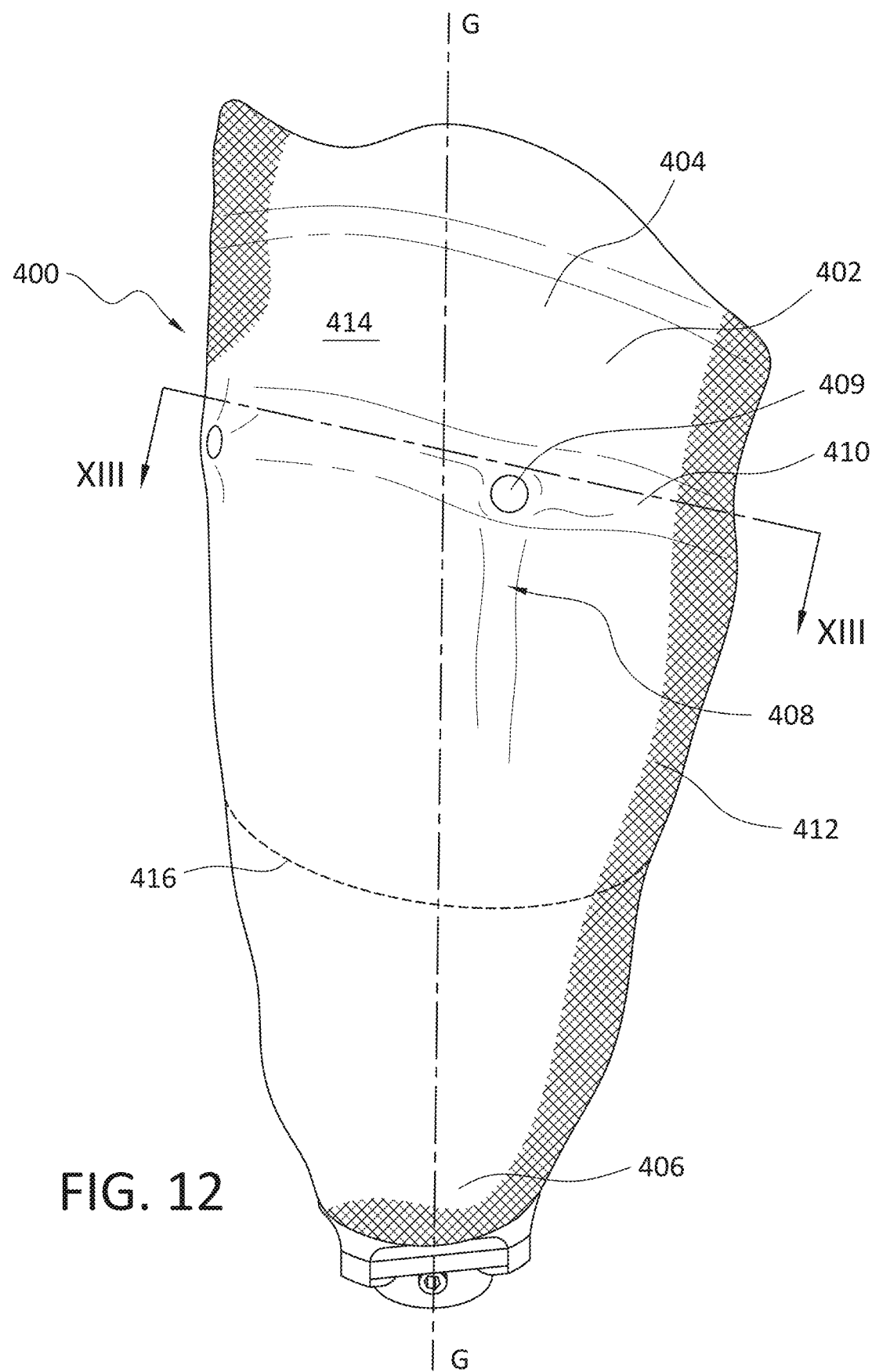
FIG. 12 is a perspective view of another embodiment of a ventilated prosthetic socket, including at least one ventilated channel.

FIG. 12 shows another embodiment of a prosthetic socket 400. The prosthetic socket 400 includes a rigid, structural and load-bearing socket body 402 in the form of a closed-ended cup defining an open-ended proximal end area 404 and a closed-end distal end area 406 along an axis G-G, as in the prosthetic socket of FIG. 1. The socket body 402 forms an inner volume adapted to receive a residual limb, and the socket body 402 defines a wall thickness from an inner surface bordering the inner volume to an outer surface.

At least one channeled portion 408 communicates the inner surface 418 to the outer surface 414 and has an opening 409 extending therebetween along the socket body to permit thereby a transfer of air from the inner volume to outside of the socket.

The at least one channeled portion 408 defines a channel 410 located along line XIII-XIII extending at least partially circumferentially with a circumferential section about the axis G-G and interconnecting a plurality of the openings 409. The channel 410 is defined along the interior surface of the socket body 402. The channel 410 may be recessed toward the outer surface 414 or into a thickness of the socket body 402 from the inner surface 418. The at least one channeled portion 408 preferably bulges away from the axis G-G and creates bulged sections 412 on the outer surface 414 of the socket body 402.

The at least one channeled portion 408 may be formed by the material forming the socket body 402. The at least one channeled portion 408 preferably is located above or proximally of a seal region 416 of the prosthetic socket.

Figure 13:
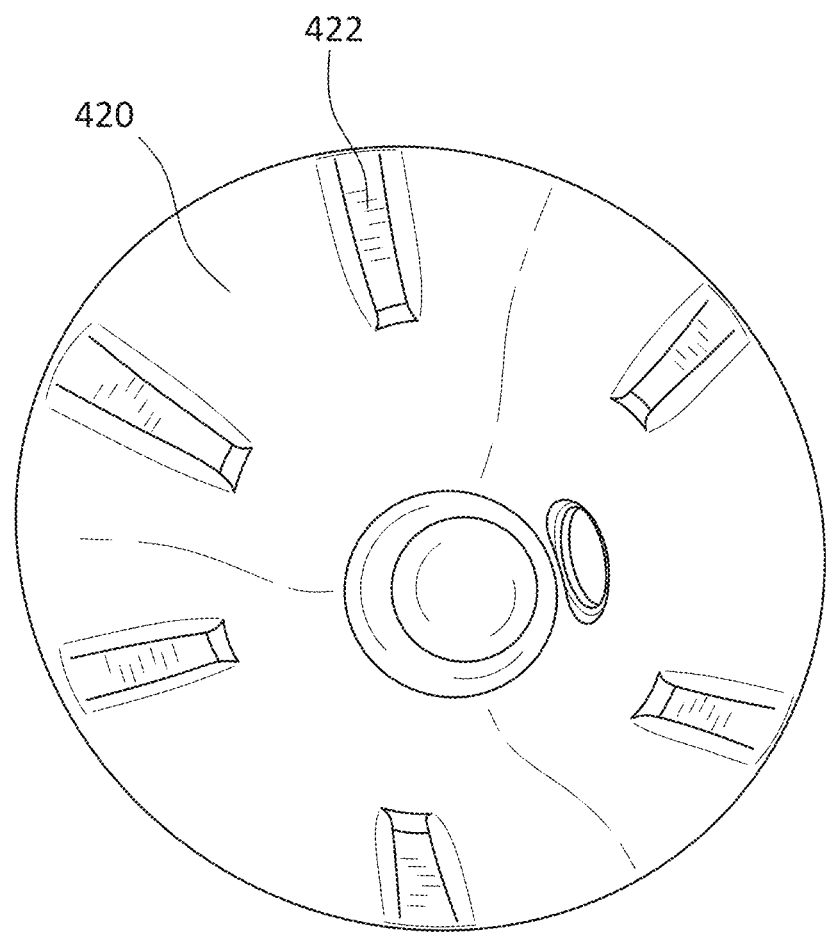
FIG. 13 is a schematic view of a template for making the at least one ventilated channel in FIG. 12.

FIG. 13 is a template 420 that can be used for forming the at least one channeled portion with protrusions 422. The template can be provided as a part of kit for making the prosthetic socket. As an alternative, removable elements may be provided with a kit for making a prosthetic socket, and such removable elements can be removed once the socket is formed to form the at least one channeled portion.

In any of the embodiments of the vent elements and corresponding prosthetic sockets, the vent elements may be combined with known methods for making prosthetic sockets for offering a ventilated socket.

Various processes make definitive sockets for fitting prostheses to residual limbs of amputees in accordance with prior art techniques. For example, numerous techniques have been developed that involve first, creating a negative mold of the residual limb, second, creating a positive mold from the negative mold, third, modifying the positive mold to provide relief for sensitive areas of the residuum, and fourth, forming the prosthesis socket using the modified positive mold. This technique involves numerous steps, and the negative and positive molds are typically created using Plaster-of-Paris. Some examples of this technique are embodied in U.S. Pat. No. 5,503,543, granted Apr. 2, 1996; and U.S. Pat. No. 6,991,444 granted Jan. 31, 2006.

Another technique used to form prosthetic sockets is to reduce the above process steps by forming the socket directly on the residual limb without creating both a negative and a positive mold. This technique can be implemented in a variety of ways. For example, U.S. Pat. No. 5,718,925, granted Feb. 15, 1998; U.S. Pat. No. 5,971,729, granted Oct. 26, 1999; U.S. Pat. No. 5,972,036, granted Oct. 26, 1999; and U.S. Pat. No. 6,416,703 granted Jul. 9, 2002, and all herein incorporated by reference, all disclose a method of forming a definitive prostheses socket directly upon a residual limb.

A web-like tubular braided carbon fiber sleeve pre-impregnated with a water curable resin is soaked in water and placed upon the residuum in a method. The sleeve is pressure cast in a known manner using the ICECAST™ system made by Ossur hf of Reykjavik, Iceland, and described in U.S. Pat. No. 5,885,509, granted Mar. 23, 1999 and herein incorporated by reference. Other methods for making a prosthetic socket are referenced to and described in U.S. Pat. No. 7,438,843, granted Oct. 21, 2008, and incorporated herein by reference.

The prosthetic socket according to the disclosed embodiments, advantageously provides a prosthetic socket having ventilation. The ability to vent a prosthetic socket while maintaining structural rigidity is advantageous, particularly if used with a suspension liner that likewise has ventilated properties.

It is to be understood that not necessarily all objects or advantages may be achieved under an embodiment of the disclosure. Those skilled in the art will recognize that the prosthetic socket and methods for making the same may be embodied or carried out in a manner that achieves or optimizes one advantage or group of advantages as taught herein without achieving other objects or advantages as taught or suggested herein.

The skilled artisan will recognize the interchangeability of various disclosed features. Besides the variations described herein, other known equivalents for each feature can be mixed and matched by one of ordinary skill in this art to construct a prosthetic liner and utilize a method for making the same under principles of the present disclosure. The skilled artisan will understand that the features described herein may be adapted to other types of prosthetic, orthopedic, medical, or other devices.

Although this disclosure describes certain exemplary embodiments and examples of ventilated prosthetic socket and kit for making the same, it will be understood by those skilled in the art that the present disclosure extends beyond the specifically disclosed prosthetic socket embodiments to other alternative embodiments and/or uses of the disclosure and obvious modifications and equivalents thereof. It is intended that the present disclosure should not be limited by the disclosed embodiments described above and may be extended to other applications that may employ the features described herein.

The invention claimed is:

1. A prosthetic socket adapted to receive a residual limb wearing a prosthetic liner as an interface between the prosthetic socket and the residual limb, the prosthetic socket comprising:
a rigid, structural, and load-bearing socket body in a form of a closed-ended cup defining an open-ended proximal end area and a closed-end distal end area, the socket body forming an inner volume adapted to receive a residual limb, the socket body defining a wall thickness from an inner wall surface bordering the inner volume to an outer wall surface, the socket body forming an opening extending through the wall thickness;
a vent element communicating the inner wall surface to the outer wall surface and extending therebetween, and only permits a transfer of air from the inner volume to outside of the prosthetic socket through the opening aside from the open-ended proximal end area, the vent element spanning across the wall thickness from the inner wall surface to the outer wall surface;
wherein the opening is located proximally above a seal region extending circumferentially about the inner wall surface of the socket body distally of the vent element, the seal region demarcating whereat a sealed volume is arranged to be formed between the inner wall surface of the prosthetic socket and the prosthetic liner within the inner volume of the socket and defined distally of the vent element;
wherein the vent element includes an exterior part and an interior part securable to one another within the opening and adapted to extend over adjacent portions of the inner and outer wall surfaces, respectively.

2. The prosthetic socket of claim 1, wherein a surface of the exterior part coupling to the interior part defines a concavely curved portion along a first cross-sectional line bisecting the exterior part defines a convexly curved portion along a second cross-sectional line perpendicular extending in a same direction to the first cross-sectional line, the concavely curved portion of the exterior part tracks a horizontal geometric cylindrical curvature of the outer wall surface while the convexly curved portion of the exterior part tracks a vertical geometric shape of the outer wall surface.

3. The prosthetic socket of claim 1, wherein the interior part defines an inner flanged rim corresponding to the inner wall surface.

4. The prosthetic socket of claim 3, wherein the interior part includes a first locking element in the form of a cylinder secured to a second locking element in the form of a boss defined by the exterior part by a snap connection with cooperating prongs.

5. The prosthetic socket of claim 4, wherein the cylinder and the boss are defined along a central axis of the vent element, the cylinder has a height corresponding to the wall thickness, wherein the inner flanged rim extends from the first locking elements.

6. The prosthetic socket of claim 4, wherein the interior part defines a circumferential rim concentric to the cylinder and is arranged to protrude towards the exterior part and engage therewith, the circumferential rim is arranged to fit against an inner periphery of and within the opening.

7. The prosthetic socket of claim 6, wherein the circumferential rim is radially outwardly spaced a predetermined distance from the cylinder and the central axis.

8. The prosthetic socket of claim 3, wherein each of the interior part and the exterior part defines a rigid ventilated structure permitting a transfer of air from the inner volume to outside the socket body, the ventilated structure is formed by a grid-like structure defining a plurality interstices.

9. The prosthetic socket of claim 8, wherein the rigid ventilated structure of the interior part spans a predetermined distance between the rim and the cylinder.

10. The prosthetic socket of claim 1, further comprising a flexible brim provided along the proximal end of the socket body, extending proximally past a peripheral edge of the socket body, and located proximally relative to the vent element.

11. A kit for making a ventilated prosthetic socket, the prosthetic socket is adapted to receive a residual wearing a prosthetic liner, the kit comprising:
   a rigid, structural and load-bearing socket body in a form of a closed-ended cup defining an open-ended proximal end area and a closed-end distal end area, the socket body forming an inner volume adapted to receive a residual limb, the socket body defining a wall thickness from an inner wall surface bordering the inner volume to an outer wall surface, the socket body forming an opening extending through the wall thickness;
   a vent element arranged to communicate the inner wall surface to the outer wall surface and extend therebetween, and only permit a transfer of air from the inner volume to outside of the prosthetic socket through the opening when the residual limb wearing a prosthetic liner is inserted into the socket body, the vent element is arranged to span across the wall thickness from the inner wall surface to the outer wall surface;
   wherein the vent element is separately formed from the socket body and discretely insertable into the opening and secured against the inner wall surface and the outer surface;
   wherein the opening is located proximally above a seal region extending circumferentially about the inner wall surface of the socket body distally of the vent element, the seal region demarcating whereat a sealed volume is arranged to be formed between the inner wall surface of the prosthetic socket and the prosthetic liner within the inner volume of the socket and defined distally of the vent element;
   wherein the vent element includes an exterior part and an interior part securable to one another within the opening and adapted to extend over adjacent portions of the inner and outer wall surfaces, respectively.

12. The kit of claim 11, further comprising a flexible brim provided along the proximal end of the socket body, extending proximally past a peripheral edge of the socket body, and located proximally relative to the vent element.

13. The kit of claim 11, wherein a surface of the exterior part coupling to the interior part defines a concavely curved portion along a first cross-sectional line bisecting the exterior part defines a convexly curved portion along a second cross-sectional line perpendicular extending in a same direction to the first cross-sectional line, the concavely curved portion of the exterior part tracks a horizontal geometric cylindrical curvature of the outer wall surface while the convexly curved portion of the exterior part tracks a vertical geometric shape of the outer wall surface.

14. The kit of claim 13, wherein the interior part defines an inner flanged rim corresponding to the inner wall surface.

15. The kit of claim 14, wherein the interior part includes a first locking element in the form of a cylinder secured to a second locking element in the form of a boss defined by the exterior part by a snap connection with cooperating prongs;
   wherein the cylinder and the boss are defined along a central axis of the vent element, the cylinder has a height corresponding to the wall thickness.

* * * * *